United States Patent [19]

Carson et al.

[11] Patent Number: 4,628,115
[45] Date of Patent: Dec. 9, 1986

[54] SUBSTITUTED 4-ACETYL-3-HYDROXYPHENOXY ALKANOIC ACIDS

[75] Inventors: Matthew Carson, Nutley; Ronald A. LeMahieu, North Caldwell; William C. Nason, Mountain Lakes, all of N.J.

[73] Assignee: Hoffmann-La Roche Inc., Nutley, N.J.

[21] Appl. No.: 715,440

[22] Filed: Mar. 25, 1985

[51] Int. Cl.$^4$ .................................................. C07L 59/76
[52] U.S. Cl. ................................... 562/464; 558/315; 514/571; 568/337; 560/53
[58] Field of Search ............... 562/461, 464; 514/571; 560/53

[56]  References Cited

FOREIGN PATENT DOCUMENTS

EP108592  5/1984  European Pat. Off. ............ 562/464
3312675  10/1983  Fed. Rep. of Germany .

*Primary Examiner*—Paul J. Killos
*Attorney, Agent, or Firm*—Jon S. Saxe; Bernard S. Leon; William G. Isgro

[57] ABSTRACT

The invention relates to compounds of the formula

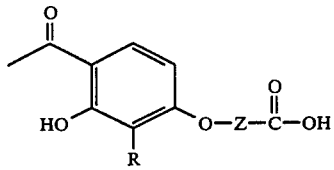

wherein R is hydrogen or lower alkyl, Z is alkylene of 1 to 10 carbon atoms, $-(C^*H_2)_3-C\equiv C-$, $-C^*H_2-C\equiv C-(CH_2)_3-$, and $-(CH_2)_2O)_n(CH_2)_2-$ wherein n is an integer of 1 to 3, the carbon atom marked with an asterisk is linked to the phenoxy moiety, and salts thereof with pharmaceutically acceptable bases. The compounds of formula I are antagonists of slow reacting substance of anaphylaxis (SRS-A; leukotrienes $C_4$, $D_4$ and $E_4$), which renders them useful as agents for the treatment of allergic conditions.

22 Claims, No Drawings

SUBSTITUTED 4-ACETYL-3-HYDROXYPHENOXY ALKANOIC ACIDS

BRIEF SUMMARY OF THE INVENTION

The invention relates to 4-acetyl-3-hydroxyphenoxy alkanoic acids of the formula

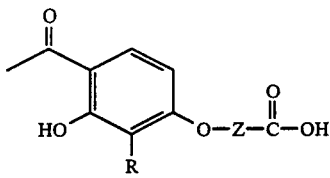

wherein R is hydrogen or lower alkyl, Z is alkylene, $-C^*H_2CH_2CH_2-C\equiv C-$, $-C^*H_2-C\equiv C-(CH_2)_3-$ and $\pm(CH_2)_2O\pm_n(CH_2)_2-$, wherein n is an integer of 1 to 3, the carbon atom marked with an asterisk is linked to the phenoxy moiety, and salts thereof with pharmaceutically acceptable bases. The compounds of formula I are antagonists of slow reacting substance of anaphylaxis (SRS-A; leukotrienes $C_4$, $D_4$ and $E_4$), which renders them useful as agents for the treatment of allergic conditions.

DETAILED DESCRIPTION OF THE INVENTION

As used herein, the term "Halo" denotes all of the halogens, that is, bromine, chlorine, fluorine and iodine. The term "lower alkyl" denotes straight or branched chain hydrocarbon moieties of 1 to 7 carbon atoms, for example, methyl, ethyl, propyl, isopropyl, butyl, isobutyl, pentyl, isopentyl, hexyl, heptyl and the like; preferred is propyl. The term "alkylene" denotes straight or branched chain hydrocarbon moieties of 1 to 10 carbon atoms, for example, methylene, ethylene, propylene, 2-methylpropylene, 2,2-dimethylpropylene, butylene, and the like; preferred are butylene, pentylene and hexylene.

The compounds of the invention characterized by following formula

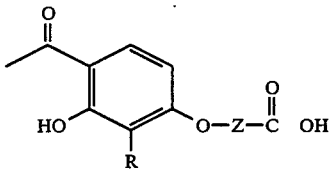

wherein R is hydrogen or lower alkyl, Z is alkylene, $-C^*H_2CH_2CH_2-C\equiv C-$, $-C^*H_2-C\equiv C-(CH_2)_3-$, and $\pm(CH_2)_2O\pm_n(CH_2)_2-$, wherein n is an integer of 1 to 3, the carbon marked with an asterisk is linked to the phenoxy moiety, and salts thereof with pharmaceutically acceptable bases, can be prepared as herein described.

Generally, the preferred compounds of formula I of the invention are those wherein R is lower alkyl and Z is butylene, pentylene or hexylene.

Most preferred compounds of the invention are the following:

5-(4-acetyl-3-hydroxy-2-propylphenoxy)pentanoic acid;
6-(4-acetyl-3-hydroxy-2-propylphenoxy)hexanoic acid;
7-(4-acetyl-3-hydroxy-2-propylphenoxy)heptanoic acid;
7-(4-acetyl-3-hydroxy-2-propylphenoxy)-2-hexynoic acid; and
6-(4-acetyl-3-hydroxy-2-propylphenoxy)-5-heptynoic acid.

Exemplary of other compounds of the invention are the following:

(4-acetyl-3-hydroxy-2-propylphenoxy)acetic acid;
3-(4-acetyl-3-hydroxy-2-propylphenoxy)propanoic acid;
4-(4-acetyl-3-hydroxy-2-propylphenoxy)butanoic acid;
8-(4-acetyl-3-hydroxy-2-propylphenoxy)octanoic acid;
9-(4-acetyl-3-hydroxy-2-propylphenoxy)nonanoic acid;
10-(4-acetyl-3-hydroxy-2-propylphenoxy)decanoic acid;
11-(4-acetyl-3-hydroxy-2-propylphenoxy)undecanoic acid;
4-(4-acetyl-3-hydroxy-2-propylphenoxy)-2,2-dimethylbutanoic acid;
4-(4-acetyl-3-hydroxy-2-propylphenoxy)-3-methylbutanoic acid;
4-(4-acetyl-3-hydroxy-2-propylphenoxy)-2-methylbutanoic acid;
6-(4-acetyl-3-hydroxy-2-propylphenoxy)-2-methylhexanoic acid;
6-(4-acetyl-3-hydroxy-2-propylphenoxy)-3-methylhexanoic acid;
6-(4-acetyl-3-hydroxy-2-propylphenoxy)-3,3-dimethylhexanoic acid;
3-[2-(4-acetyl-3-hydroxy-2-propylphenoxy)ethoxy]propanoic acid;
3-[2-[2-[2-(4-acetyl-3-hydroxy-2-propylphenoxy)ethoxy]ethoxy]ethoxy]propanoic acid; and the like.

The compounds of formula I of the invention can be prepared as hereinafter specifically set forth in Reaction Schemes I-V.

REACTION SCHEME I

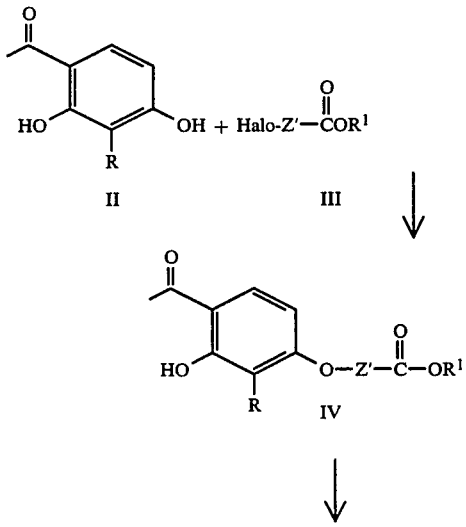

-continued
REACTION SCHEME I

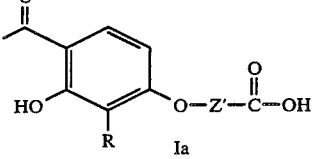

wherein $R^1$ is lower alkyl, $Z'$ is $CH_2$, $(CH_2)_{3-10}$, and R is as previously described.

In Reaction Scheme I, the reaction between a compound of formula II and III, which are known compounds, is carried out in an inert solvent, for example, a ketone, preferably acetone or methyl ethyl ketone, or dimethyl formamide, in the presence of a base, such as, an alkali metal carbonate, preferably potassium carbonate. The reaction is carried out at a temperature in the range of from about 50° to about 100° C. The obtained ester of formula IV is converted to the corresponding compound of formula Ia of the invention by hydrolysis, with an alkali metal hydroxide such as sodium hydroxide in an aqueous alcohol, for exmple, methanol or ethanol at a temperature in the range of from about 25° to about the boiling point of the reaction mixture. The obtained compound of formula Ia can be separated by known procedures, for example, crystallization, chromatography and the like.

wherein $Z''$ is $-(CH_2)_{3-10}-$, or $-[(CH_2)_2O]_n(CH_2)_2-$, Halo is halogen, and R is as previously described.

In Reaction Scheme II, a compound of formula II, which are known compounds, is allowed to react with an excess of a dihalo compound of formula V in the presence of an alkali metal carbonate, preferably protassium carbonate, in a solvent such as acetone, methyl ethyl ketone or dimethyl formamide. The reaction is carried out at a temperature in the range of from about 50° to about 100° C. The halo compound of formula VII that is obtained is then allowed to react with an alkali metal cyanide such as sodium cyanide in a solvent such as dimethyl formamide at a temperature in the range of from about 50° to about 100° C. to give the nitrile of formula VIII. Alternatively, the nitrile of formula VIII may be prepared directly from a compound of formula II. A compound of formula II is allowed to react with a halo nitrile of formula VI in a solvent such as acetone or dimethyl formamide in the presence of a base such as potassium carbonate at elevated temperatures in the range of from about 50° to about 100° C. A nitrile of formula VIII may be converted to a corresponding compound of the invention of formula Ib by the following sequence of steps. Treatment of a compound of formula VIII with hydrogen chloride in methanol at temperatures in the range of from about 0° to about 25° C. followed by water provides a methyl ester which is hydrolyzed with an alkali metal hydroxide in an alcohol solvent. The obtained compound of formula Ib can be separated by known procedures, for example, crystallization, chromatography and the like.

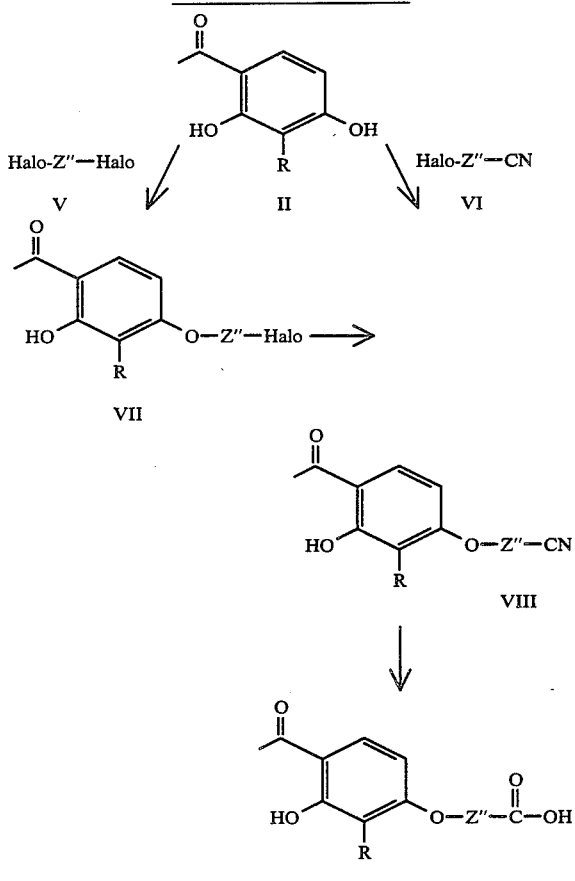

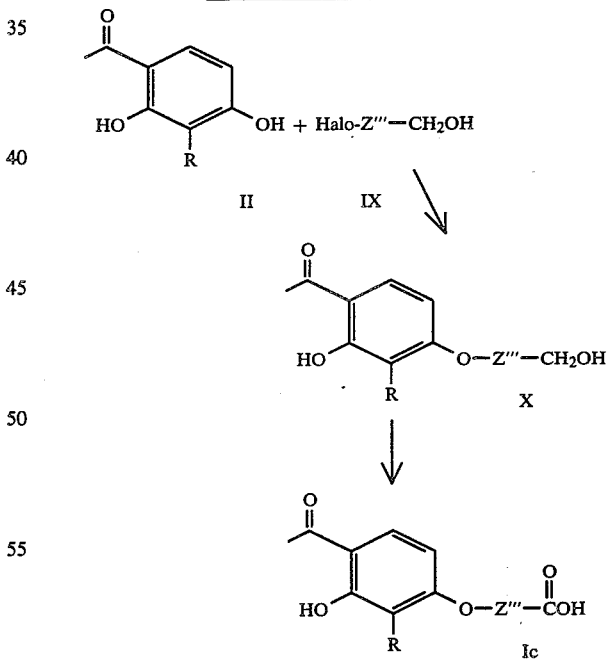

wherein $Z'''$ is $-(CH_2)_{2-10}-$, and Halo and R are as previously described.

In Reaction Scheme III, a compound of formula II, which are known compounds, is alkylated with a halo alcohol of formula IX in a solvent such as acetone or dimethylformamide in the presence of a base such as an alkali metal carbonate, preferably potassium carbonate, at a temperature in the range of from about 50° to about 100° C. An alkali metal iodide may be used to facilitate the reaction. The product obtained of formula X is then oxidized under standard Jones oxidation conditions, which comprise treatment with chromium trioxide and sulfuric acid in an inert solvent such as acetone at a temperature in the range of about 0° to 25° C. This provides the corresponding compound of formula Ic of the invention. The obtained compound of formula IC can be separated by known procedures, for example, crystallization, chromatography and the like.

The oxidation of a compound of formula XIII to the corresponding compound of formula Id is carried out by treatment of the compound of formula XIII with the Jones reagent, that is, chromium trioxide in 10N sulfuric acid, using a solvent such as acetone or methyl ethyl ketone at a temperature in the range of from about 0° to about 30° C.

A compound of formula I, wherein Z is —CH$_2$C≡C(CH$_2$)$_3$—, can be prepared as hereinafter set forth in Reaction Scheme V.

REACTION SCHEME V

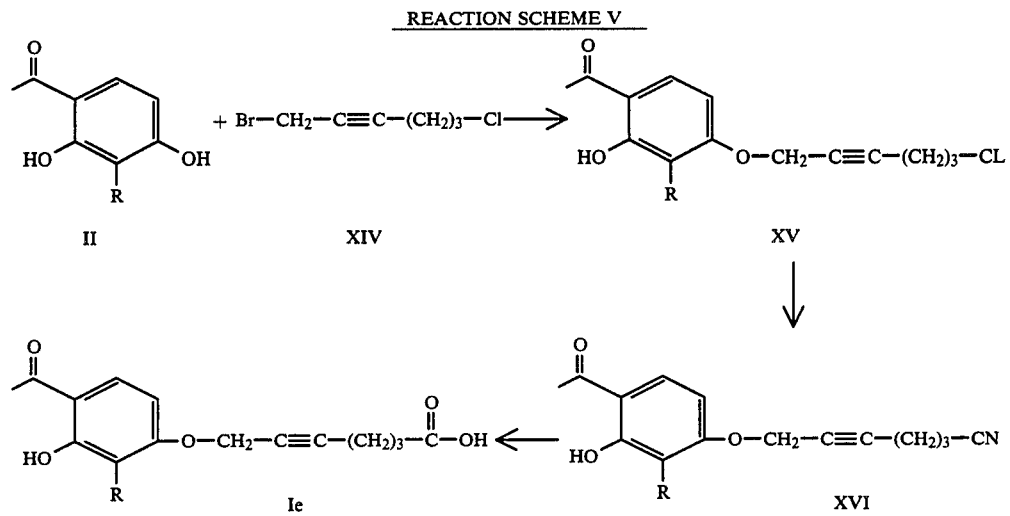

A compound of formula I, wherein Z is —(CH$_2$)$_3$—C≡C—, can be prepared as hereinafter set forth in Reaction Scheme IV In Reaction Scheme V, the reaction between a compound of formula II and XIV, which are known compounds, is carried out in an inert solvent, for example, a

REACTION SCHEME IV

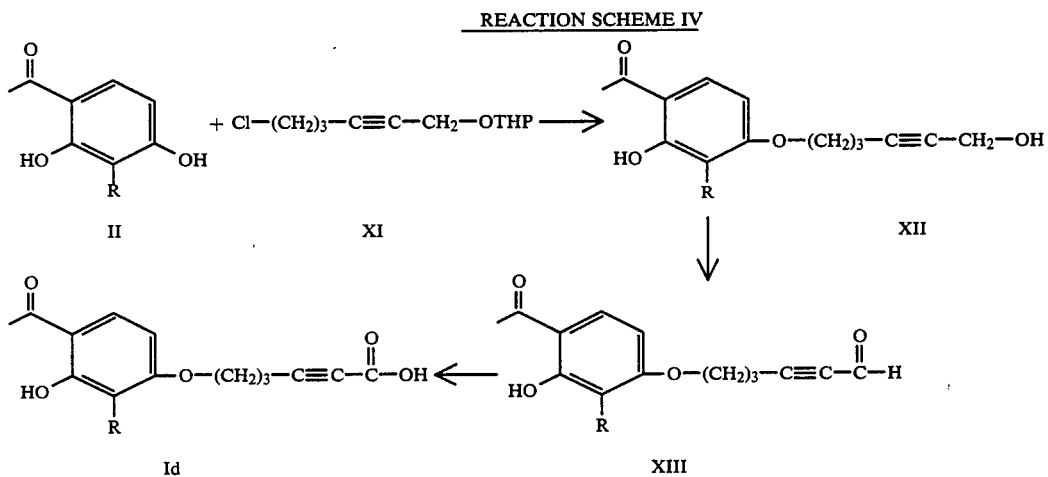

In Reaction Scheme IV, the reaction between a compound of formula II and XI, which are known compounds, is carried out in an inert solvent, for example, a ketone, preferably acetone or methyl ethyl ketone, or dimethyl formamide, in the presence of a base such as an alkali metal carbonate, perferably potassium carbonate. The reaction is carried out at temperature in the range of from about 25° to about 100° C. The oxidation of a compound of formula XII to the corresponding compound of formula XIII is carried out by stirring with activated manganese dioxide in an inert chlorinated hydrocarbon solvent such as methylene chloride or chloroform at 0°-30° C.

ketone, preferably acetone or methyl ethyl ketone, or dimethyl formamide in the presence of a base such as an alkali metal carbonate, preferably potassium carbonate. The reaction is carried out at a temperature in the range of from about 25° to about 100° C.

The corresponding compound of formula XV that is obtained is then allowed to react with an alkali metal cyanide such as sodium cyanide in the presence of sodium iodide in a solvent such as dimethylformamide at a temperature in the range of from about 50° to about 100° C. to give the corresponding compound of formula XVI.

The nitrile of formula XVI is hydrolyzed to Ie by treatment with an alkali metal hydroxide such as sodium hydroxide in a solvent such as ethylene glycol or propylene glycol at an elevated temperature in the range of from about 80° to about 150°.

The invention also relates to the pharmaceutically acceptable salts of the compounds of formula I. Said salts can be prepared by reacting an acid of formula I with a base having a non-toxic, pharmacologically and pharmaceutically acceptable cation. In general, any base which will form a salt with a carboxylic acid and whose pharmacological properties will not cause an adverse physiological effect when ingested by a warmed blooded animal is considered as being within the scope of this invention. Suitable bases thus include, for example, the alkali metal and alkaline earth metal hydroxides, carbonates, for example, sodium hydroxide, potassium hydroxide, calcium hydroxide, potassium carbonate and the like, ammonia, primary, secondary and tertiary amines, such as monoalkylamines, dialkylamines, trialkylamines, nitrogen containing heterocyclic amines, for example, piperidine, amino acids such as lysine, and the like. The pharmaceutically acceptable salts thus produced are the functional equivalent of the corresponding 4-acetyl-3-hydroxyphenoxy alkanoic acid of formula I and one skilled in the art will appreciate that, to the extent that the salts of the invention are useful in therapy, the variety of salts encompassed by this invention are limited only by the criterion that the bases employed in forming the salts be both non-toxic and physiologically acceptable.

The compounds of formula I of the invention are useful in the treatment of disorders in which slow reacting substance of anaphylaxis (SRS-A; leukotrienes $C_4$, $D_4$, and $E_4$) is a mediator. The compounds of formula I are therefore useful in the treatment of allergic disorders which include skin afflictions, hay fever, chronic bronchitis, obstructive airways diseases such as asthma, allergic conditions of the eye, and allergic conditions of the gastro-intestinal tract, such as food allergies.

The useful anti-allergic activity of the compounds of formula I and their stals is demonstrated in vitro and in warm-blooded animals utilizing standard procedures. Exemplary of such procedures are:

(a) Guinea Pig Illeum, In Vitro

The guinea pig ileum bioassay system has been described by Orange and Austen, Adv. Immunol. 10: 105–144 (1959). A 1.5 cm segment is removed from animals weighing 300–400 g. and suspended in an organ bath containing 10 ml. of Tyrodes solution with $10^{-6}$M atropine sulfate and $10^{-6}$M pyrilamine maleate. The bath is maintained at 37° C. and aerated with a mixture of 95% oxygen and 5% carbon dioxide. The SRS-A utilized in this screen is obtained by challenging chopped lung fragments from actively sensitized guinea pigs with egg albumin, in vitro. A dose-response curve to SRS-A challenge is established for the ileum. The dose of SRS-A which gives 50% of the maximal contraction ($EC_{50}$) is then used for subsequent challenge. The drug concentration which inhibits, by 50%, the SRS-A induced constriction of the guinea pig ileum is determined. In this bioassay system the standard SRS-A antagonist, 7-[3-(4-acetyl-3-hydroxy-2-propylphenoxy)-2-hydroxypropoxy]-4-oxo-8-propyl-4H-1-benzopyran-2-carboxylic acid, has an $IC_{50}$ of $3.5 \times 10^{-8}$M. Results obtained with representative compounds of the present invention is this assay are summarized hereafter in TABLE 1.

TABLE I

In vitro SRS—A Antagonism Test

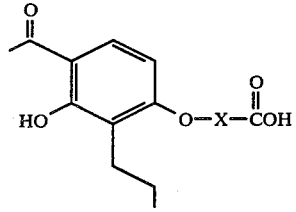

| X | Guinea Pig Ileum $IC_{50}$(M) |
|---|---|
| $CH_2$ | $10^{-5}$ |
| $(CH_2)_2$ | $10^{-5}$ |
| $(CH_2)_3$ | $1 \times 10^{-5}$ |
| $(CH_2)_4$ | $5 \times 10^{-6}$ |
| $(CH_2)_5$ | $1 \times 10^{-6}$ |
| $(CH_2)_6$ | $5 \times 10^{-6}$ |
| $(CH_2)_7$ | $5 \times 10^{-6}$ |
| $(CH_2)_{10}$ | $10^{-5}$ |
| $(CH_2)_3C \equiv C$ | $1 \times 10^{-6}$ |
| $CH_2C \equiv C(CH_2)_3$ | $1 \times 10^{-6}$ |
| $(CH_2)_2O(CH_2)_2$ | $5 \times 10^{-6}$ |
| $(CH_2)_2O(CH_2)_2O(CH_2)_2O(CH_2)_2$ | $6 \times 10^{-6}$ |

(b) Guinea Pig Bronchoconstriction, In Vivo

Male guinea pigs (Hartley strain) weighing 300 to 450 grams are anesthetized with urethane (2 g/Kg) intraperitoneally and a polyethylene cannula is inserted into the jugular vein for intravenous drug administration. Tracheal pressure is recorded from a cannula inserted in the trachea and connected to a Statham pressure transducer. Respiration is paralyzed with succinyl choline (1.2 mg/kg, i.v.) and the animals are mechanically respirated (Howard rodent respirator) at 40 breaths/minute and 2.5 cc tidal volume. The minutes thereafter, propranolol (0.1 mg/kg, i.v.) is administered. Five minutes later, the animals are pretreated intravenously for 30 seconds (at 10 mg/kg) with test drug or control vehicle. The animals are subsequently challenged with a maximally constrictory dose of leukotriene $E_4$ also administered intravenously. The change (cm $H_2O$) between pre and peak ventilatory pressure readings is averaged calculated from the following formula:

$$\frac{\text{Control-Drug Treated}}{\text{Control}} \times 100.$$

7-[2-(4-Acetyl-3-hydroxy-2-propylphenoxy)-2-hydroxypropoxy]-4-oxo-8-propyl-4H-1-benzopyran-2-carboxylic acid elicits a 98% inhibition at 10 mg/kg, i.v., in this test. A representative compound of the present invention, i.e., 6-(4-acetyl-3-hydroxy-2-propylphenoxy)hexanoic acid, caused a 73% inhibition at 10 mg/kg i.v. in this test.

(c) Rat Skin Permeability, in Vivo

In this model the ability of $LTE_4$ to increase vascular permeability in rat skin was utilized. Anesthetized rats, pretreated for 30 minutes with an antihistamine, pyrilamine maleate, (50 mg/kg i.p.) and a serotonin antagonist, methylsergide maleate (4 mg/kg i.p.), were injected intradermally with a dose of $LTE_4$ which gave a maximum wheal (in 0.05 ml saline). After introduction of test drug (at 10 mg/kg, i.v.) the animals were immediately treated intravenously with Evans blue dye i.v. (0.5%) in the tail vein resulting in the formation of a skin wheal. Thirty minutes later the animals were sacrificed and the skin wheal size was measured. The average response in 5 animals (4 intradermal injections per animal) treated with test compound was compared to that obtained in a similar group of control animals to determine the percent inhibition by the drug. A representative compound of the present invention, i.e., 6-(4-acetyl-3-hydroxy-2-propylphenoxy)hexanoic acid, caused a 35% reduction in skin wheal when tested at 10 mg/kg i.v.

(d) Aerosol Test

Male guinea pigs (Hartley strain) weighing 300 to 500 g are anesthetized with urethane (2 g/kg) intraperitoneally and a polyethylene cannula is inserted into the jugular vein for test compound administration. Tracheal pressure is recorded from a cannula inserted in the trachea and connected to a Statham pressure transducer. After surgical preparation of the animals, a period of time is allowed for pulmonary functions to stabilize. For testing purposes, drugs are administered according to the following protocol. Propranolol (0.1 mg/kg) is administered intravenously while the animals breathed spontaneously. Five minutes thereafter, the animals are exposed for a five minute period to a 1% (W/V) aerosol solution of test compound (adjusted to an alkaline pH where necessary for compound solubilization) or to distilled water of the appropriate pH (for control purposes). A Monaghan (Model 750) ultrasonic nebulizer is used to administer all compounds by inhalation. Aqueous solutions are prepared fresh and introduced into the chamber of the nebulizer. The output of the nebulizer is made available to the animal by directing a bias flow of aerosol through a y tube connected to the tracheal cannula. At the end of the exposure period, the animals are paralyzed with succinylcholine (1.2 mg/kg, i.v.) and mechanically respirated (Harvard rodent respirator) at 40 breaths/min and 2.5 cc tidal volume. Animals are then challenged with a maximum constrictory dose of LTE$_4$ delivered intravenously 30 seconds after administration of the succinylcholine. A representative compound of the present invention, i.e., 6-(4-acetyl-3-hydroxy-2-propylphenoxy)hexanoic acid, caused a 36% inhibition of the bronchoconstriction.

A compound of formula I, or a salt thereof, or a composition containing a therapeutically effective amount of a compound of formula I, or a salt thereof can be administered by methods well known in the art. Thus, a compound of formula I, or a salt thereof can be administered either singly or with other pharmaceutical agents, for example, antihistamines, mediator release inhibitors, methyl xanthines, B$_2$ agonists or antiasthmatic steroids such as prednisone and prednisolone, orally, parenterally, rectally or by inhalation, for example, in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or water or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

In the practice of the invention, the dose of a compound of formula I or a salt thereof to be administered and the frequency of administration will be dependent on the potency and duration of activity of the particular compound of formula I or salt to be administered and on the route of administration, as well as the severity of the condition, age of the mammal to be treated and the like. Doses of a compound of formula I or a salt thereof contemplated for use in practicing the invention are in the range of from about 25 to about 1000 mg per day, preferably about 25 to about 250 mg either as a single dose or in divided doses.

The Examples which follow further illustrate the invention. All temperatures are in degrees centigrade, unless otherwise stated.

EXAMPLE 1

Preparation of (4-Acetyl-3-hydroxy-2-propylphenoxy)acetic acid ethyl ester

A mixture of 24.25 g of 1-(2,4-dihydroxy-3-propylphenyl)ethanone, 16.0 ml of ethyl chloroacetate and 26 g anhydrous potassium carbonate in 375 ml of anhydrous acetone was stirred at reflux for 17 hours. The reaction mixture was filtered and the filtrate was concentrated in vacuo to an oil which was crystallized from ethanol to give 27.2 g of (4-acetyl-3-hydroxy-2-propylphenoxy)acetic acid ethyl ester, the titled compound, mp 61°-64°, (78% yield) in two crops.

Analysis Calculated for $C_{15}H_{20}O_5$: C, 64.27; H, 7.19. Found: C, 64.10; H, 7.12.

EXAMPLE 2

Preparation of (4-Acetyl-3-hydroxy-2-propylphenoxy)acetic acid.

To 5.6 g of (4-acetyl-3-hydroxy-2-propylphenoxy)acetic acid ethyl ester in 50 ml of methanol was added 50 ml of 1.0N sodium hydroxide and the solution was stirred at reflux for 2 hours. The methanol was removed in vacuo, the residue was acidified and the product was extracted with ether. The dried (over magnesium sulfate) extract was concentrated in vacuo to a solid which was recrystallized from ether-hexane to give 4.18 g of (4-acetyl-3-hydroxy-2-propylphenoxy)acetic acid, the titled compound, mp 128°-130°, (83% yield).

EXAMPLE 3

Preparation of 1-[2-Hydroxy-4-(3-hydroxypropoxy)-3-propylphenyl]ethanone

A mixture of 5.80 g of 1-(2,4-dihydroxy-3-propylphenyl)ethanone, 3.6 ml of 3-bromo-1-propanol and 8.3 g of anhydrous potassium carbonate in 50 ml of anhydrous dimethyl formamide was stirred at 75° for 64 hours. The reaction mixture was concentrated in vacuo, the residue was acidified and extracted with ethyl acetate. The extract was dried over magnesium sulfate and concentrated in vacuo to 8.7 g of an oil which was chromatographed on 150 g of silica gel. Elution with 40% ethyl acetate-toluene gave 2.84 g which was crystallized from ether-hexane to yield 2.14 g, mp 57°–59°, (28% yield) of 1-[2-hydroxy-4-(3-hydroxypropoxy)-3-propylphenyl]ethanone, the titled compound.

Analysis Calculated for $C_{14}H_{20}O_4$: C, 66.65; H, 7.99. Found: C, 66.56; H, 7.99.

Additional fractions (1.42 g) of slightly impure product were obtained.

EXAMPLE 4

Preparation of 3-(4-Acetyl-3-hydroxy-2-propylphenoxy)propanoic acid

A solution of 2.00 g of 1-[2-hydroxy-4-(3-hydroxypropoxy)-3-propylphenyl]ethanone in 30 ml of acetone was added dropwise over 45 minutes to a stirred, ice cooled solution of 4.0 ml of Jones reagent in 10 ml of acetone. After 15 additional minutes, the cooling bath was removed and the reaction mixture was stirred at 23° for 15 minutes. Jones reagent (0.5 ml) was added and stirring was continued for 15 minutes. The reaction mixture was concentrated in vacuo and the residue was treated with water and extracted with ether. The ether extract was washed with three portions of 1N sodium hydroxide and the aqueous layers were combined and acidified. The product was extracted with ether and the dried (over magnesium sulfate) extract was concentrated in vacuo to a solid (1.48 g). Recrystallization from ether-hexane gave 1.21 g, mp 142°–146°, (57% yield) of 3-(4-acetyl-3-hydroxy-2-propylphenoxy)propanoic acid, the titled compound.

Analysis Calculated for $C_{14}H_{18}O_5$: C, 63.15; H, 6.18. Found: C, 62.95; H, 7.01.

EXAMPLE 5

Preparation of 4-(4-Acetyl-3-hydroxy-2-propylphenoxy)butanoic acid ethyl ester A mixture of 2.91 g of 1-(2,4-dihydroxy-3-propylphenyl)ethanone, 2.91 g of ethyl 4-bromobutyrate and 3.1 g of anhydrous potassium carbonate in 35 ml of anhydrous dimethyl formamide was stirred and heated at 75° for 12 hours. The solvent was removed in vacuo, the residue was treated with water and the product was extracted with ethyl acetate. The dried (over magnesium sulfate) extract was concentrated in vacuo and the crude product was purified by chromatography on 200 g of silica gel. Elution with 5% ethyl acetate-toluene gave 2.55 g (54% yield) of 4-(4-acetyl-3-hydroxy-2-propylphenoxy)butanoic acid ethyl ester, the titled compound, as an oil.

Analysis Calculated for $C_{17}H_{24}O_5$: C, 66.21; H, 7.84. Found: C, 66.33; H, 8.00.

EXAMPLE 6

Preparation of 4-(4-Acetyl-3-hydroxy-2-propylphenoxy)butanoic acid

A solution of 2.45 g of 4-(4-acetyl-3-hydroxy-2-propylphenoxy)butanoic acid ethyl ester in 40 ml of methanol and 40 ml of 1.0N sodium hydroxide was heated at reflux for 10 minutes. The methanol was removed in vacuo, the residue was acidified and the product was extracted with ether. The dried (over magnesium sulfate) extract was concentrated in vacuo and the solid residue was recrystallized from ethher-hexane to give 1.95 g (87% yield), mp 130°–133°, of 4-(4-acetyl-3-hydroxy-2-propylphenoxy)butanoic acid, the titled compound.

Analysis Calculated for $C_{15}H_{20}O_5$: C, 64.27; H, 7.19. Found: C, 64.09; H, 7.38.

EXAMPLE 7

Preparation of 5-(4-Acetyl-3-hydroxy-2-propylphenoxy)pentanoic acid methyl ester A mixture of 2.92 g of 1-(2,4-dihydroxy-3-propylphenyl)ethanone, 2.91 g of methyl 5-bromopentanoate and 3.1 g of anhydrous potassium carbonate in 35 ml of anhydrous dimethyl formamide was stirred and heated at 75° for 16 hours. The usual workup followed by chromatography on 350 g of silica gel and elution with 5% ethyl acetate-toluene gave 3.07 g (66% yield) of 5-(4-Acetyl-3-hydroxy-2-propylphenoxy)pentanoic acid methyl ester, the titled compound, as an oil.

Analysis Calculated for $C_{17}H_{24}O_5$: C, 66.21; H, 7.85. Found: C, 66.39; H, 7.80.

EXAMPLE 8

Preparation of 5-(4-Acetyl-3-hydroxy-2-propylphenoxy)pentanoic acid

A solution of 2.97 g of 5-(4-acetyl-3-hydroxy-2-propylphenoxy)pentanoic acid methyl ester in 50 ml of methanol and 50 ml of 1.0N sodium hydroxide was heated at reflux for 10 minutes. The usual workup followed by recrystallization from ether-hexane gave 2.69 g (95% yield), mp 97°–102°, of 5-(4-Acetyl-3-hydroxy-2-propylphenoxy)pentanoic acid, the titled compound.

Analysis Calculated for $C_{16}H_{22}O_5$: C, 65.29; H, 7.53. Found: C, 65.46; H, 7.77.

EXAMPLE 9

Preparation of 6-(4-Acetyl-3-hydroxy-2-propylphenoxy)hexanoic acid methyl ester A mixture of 2.72 g of 1-(2,4-dihydroxy-3-propylphenyl)ethanone, 2.72 g of methyl 6-bromohexanoate and 2.90 g of anhydrous potassium carbonate in 30 ml of anhydrous dimethyl formamide was stirred and heated at 75° for 7 hours. The usual workup followed by chromatography on 200 g of silica gel and elution with 10% ethyl acetate-toluene gave 2.77 g (62% yield) of 6-(4-Acetyl-3-hydroxy-2-propylphenoxy)hexanoic acid methyl ester, the titled compound, as an oil.

Analysis Calculated for $C_{18}H_{26}O_5$: C, 67.06; H, 8.13. Found: C, 66.92; H, 8.25.

EXAMPLE 10

Preparation of 6-(4-Acetyl-3-hydroxy-2-propylphenoxy)hexanoic acid

A solution of 1.40 g of 6-(4-acetyl-3-hydroxy-2-propylphenoxy)hexanoic acid methyl ester in 20 ml of methanol and 22 ml of 1.0N sodium hydroxide was stirred at reflux for 10 minutes. The usual workup followed by recrystallization from ether-hexane gave 1.10 g (82%) yield), mp 62°–64°, of 6-(4-Acetyl-3-hydroxy-2-propylphenoxy)hexanoic acid, the titled compound.

Analysis Calculated for $C_{17}H_{24}O_5$: C, 66.21; H, 7.84. Found: C, 65.97; H, 7.95.

EXAMPLE 11

Preparation of 8-(4-Acetyl-3-hydroxy-2-propylphenoxy)octanoic acid methyl ester A mixture of 4.30 g of 1-(2,4-dihydroxy-3-propylphenyl)ethanone, 5.10 g of methyl 8-bromooctanoate and 4.55 g of anhydrous potassium carbonate in 100 ml of anhydrous acetone and 30 ml of anhydrous dimethyl formamide was stirred at reflux for 20 hours. The usual workup followed by purification by high pressure liquid chromatography using a solvent of 15% ethyl acetate-hexane gave 4.5 g (58% yield) of 8-(4-acetyl-3-hydroxy-2-propylphenoxy)octanoic acid methyl ester, the titled compound, mp 39°–41°, after crystallization from hexane.

Analysis Calculated for $C_{20}H_{30}O_5$: C, 68.55; H, 8.63. Found: C, 68.62; H, 8.81.

EXAMPLE 12

Preparation of 8-(4-Acetyl-3-hydroxy-2-propylphenoxy)octanoic acid

A solution of 4.50 g of 8-(4-acetyl-3-hydroxy-2-propyl phenoxy)octanoic acid methyl ester in 60 ml of methanol and 50 ml of 0.1N sodium hydroxide was refluxed for 7 minutes. The usual workup followed by purification by high pressure liquid chromatography gave 2.3 g (33% yield), mp 73°–76°, of 8-(4-acetyl-3-hydroxy-2-propylphenoxy)octanoic acid, the titled compound.

Analysis Calculated for $C_{19}H_{28}O_5$: C, 67.83; H, 8.39. Found: C, 67.70; H, 8.25.

1.5 g of the starting methyl ester was also recovered in this experiment.

EXAMPLE 13

Preparation of 11-(4-Acetyl-3-hydroxy-2-propylphenoxy)undecanoic acid methyl ester A mixture of 1.00 g of 1-(2,4-dihydroxy-3-propylphenyl)ethanone, 1.44 g of methyl 11-bromoundecanoate and 1.00 g of anhydrous potassium carbonate in 20 ml of anhydrous dimethyl formamide was stirred and heated at 75° for 2 hours. The usual workup followed by chromatography on 30 g of silica gel and elution with 10% ethyl acetate-toluene gave 1.48 g (76% yield) of 11-(4-Acetyl-3-hydroxy-2-propylphenoxy)undecanoic acid methyl ester, the titled compound, as an oil.

Analysis Calculated for $C_{23}H_{36}O_5$: C, 70.38; H, 9.24. Found: C, 70.37; H, 9.36.

EXAMPLE 14

Preparation of 11-(4-Acetyl-3-hydroxy-2-propylphenoxy)undecanoic acid

A suspension of 1.38 g of 11-(4-acetyl-3-hydroxy-2-propylphenoxy)undecanoic acid methyl ester in 20 ml of methanol and 18 ml of 1.0N sodium hydroxide was stirred at 23° for 2 hours and then at reflux for 10 minutes. The usual workup followed by crystallization from ether-hexane gave 1.15 g (87% yield), mp 57°–58°, of 11-(4-acetyl-3-hydroxy-2-propylphenoxy)undecanoic acid, the titled compound.

Analysis Calculated for $C_{22}H_{34}O_5$: C, 69.81; H, 9.05. Found: C, 69.92; H, 9.14.

EXAMPLE 15

Preparation of 1-[2-Hydroxy-4-[(6-hydroxy-4-hexynyl)oxy]-3-propylphenyl]ethanone A mixture of 9.77 g of 1-(2,4-dihydroxy-3-propylphenyl)ethanone, 10.90 g of 1-(tetrahydro-2-pyranoxy)-6-chloro-2-hexyne [R. B. Moffet, P. H. Seay and W. R. Reid, J. Med. Pharm. Chem., 14, 1075 (1971)]. 10.43 g of anhydrous potassium carbonate and 8.36 g of potassium iodide in 250 ml of anhydrous acetone was stirred at reflux for 18 hours. Anhydrous dimethyl formamide (100 ml) was added and reflux with stirring was continued for 52 hours. The solvent was removed in vacuo, the residue was stirred with hexane and filtered. The filtrate was concentrated in vacuo to an oil which was dissolved in 300 ml of methanol and 200 ml of 3N hydrochloric acid and heated on the steam bath for 45 minutes. As the solvent was being removed in vacuo, crystallization occurred. Water was added and the solid was filtered to give 11.78 g, mp 88°–90°, (81% yield) of 1-[2-hydroxy-4-[(6-hydroxy-4-hexynyl)oxy]-3-propylphenyl]ethanone, the titled compound.

Analysis Calculated for $C_{17}H_{22}O_4$: C, 70.32; H, 7.64. Found: C, 70.18; H, 7.87.

EXAMPLE 16

Preparation of 6-(4-Acetyl-3-hydroxy-2-propylphenoxy)-2-hexynal

To 2.07 g of 1-[2-hydroxy-4-[(6-hydroxy-4-hexynyl)oxy]-3-propylphenyl]ethanone in 150 ml of methylene chloride at 25° was added 20.7 g of activated manganese oxide and the mixture was stirred for 2 hours. After filtration, the filtrate was concentrated in vacuo to yield 1.50 g (73% yield) of the titled compound.

Analysis Calculated for $C_{17}H_{20}O_4$: C, 70.81; H, 6.99. Found: C, 70.96; H, 6.87.

EXAMPLE 17

Preparation of 6-(4-Acetyl-3-hydroxy-2-propylphenoxy)-2-hexynoic acid

To 0.58 g of chromium trioxide in 8 ml of 10N sulfuric acid cooled at 0° was added a solution in 1.51 g of 6-(4-acetyl-3-hydroxy-2-propylphenoxy)-2-hexynal in 15 ml of acetone over 30 minutes with stirring. The reaction mixture was allowed to warm to 25° over 30 minutes and then concentrated in vacuo to remove the acetone. Water (50 ml) was added and the product was extracted with ether. The ether phase was extracted with 1.0N sodium hydroxide, the aqueous layer was separated, acidified and extracted with ether. The dried (over sodium sulfate) extract was concentrated in vacuo to a solid which was crystallized twice from ether-hexane to give 0.63 g, mp 115°–116°, (40% yield) of 6-(4-Acetyl-3-hydroxy-2-propylphenoxy)-2-hexynoic acid, the titled compound.

EXAMPLE 18

Preparation of 6-(4-Acetyl-3-hydroxy-2-propylphenoxy)-1-chloro-4-hexyne

A mixture of 3.10 g of 1-(2,4-dihydroxy-3-propylphenyl)ethanone, 3.13 g of 1-bromo-6-chloro-2-hexyne and 3.30 g of anhydrous potassium carbonate in 35 ml of anydrous acetone was stirred at reflux for 2.5 hours. The solvent was removed in vacuo, water was added to the residue and the pH was adjusted to 4.0. The product was extracted with ether and the dried (over magnesium sulfate) extract was chromatographed on 250 g of silica gel. Elution with 25% ethyl acetate-hexane gave 4.30 g (88% yield) of 6-(4-acetyl-3-hydroxy-2-propylphenoxy)-1-chloro-4-hexyne, the titled compound.

EXAMPLE 19

Preparation of 7-(4-Acetyl-3-hydroxy-2-propylphenoxy)-5-hexynenitrile

A solution of 3.98 g of 6-(4-acetyl-3-hydroxy-2-propylphenoxy)-1-chloro-4-hexyne, 0.95 g of sodium cyanide and 1.90 g of sodium iodide in 125 ml of anhydrous dimethylformamide was stirred and heated at 80° for 3 hr. The solvent was removed in vacuo, water was added to the residue and the product was extracted with ether. The dried (over magnesium sulfate) extract was chromatographed on 250 g of silica gel and eluted with 20% ethyl acetate-hexane to give 2.73 g (71% yield) of 7-(4-acetyl-3-hydroxy-2-propylphenoxy)-5-hexynenitrile, the titled compound as an oil.

Analysis Calculated for $C_{18}H_{21}NO_3$: C, 72.22; H, 7.07; N, 4.68. Found: C, 71.94; H, 6.98; N, 4.76.

EXAMPLE 20

Preparation of 7-(4-Acetyl-3-hydroxy-2-propylphenoxy)-5-heptynoic acid

A solution of 2.36 g of 7-(4-acetyl-3-hydroxy-2-propylphenoxy)-5-hexynenitrile and 47 ml of 5.0N sodium hydroxide in 95 ml of ethylene glycol was stirred and heated at 140° for 1 hour. After cooling, 300 ml of water was added, the pH was adjusted to 2.0 and the product was extracted with ether. The extract was washed twice with water, dried (MgSO₄) and concentrated in vacuo to a solid which was crystallized fom ether-hexane to yield 2.03 g, mp 84°-86°, (81% yield) of 7-(4-acetyl-3-hydroxy-2-propylphenoxy)-5-heptynoic acid, the title compound.

Analysis Calculated for $C_{18}H_{22}O_5$: C, 67.91; H, 6.97. Found: C, 67.92; H, 6.88.

EXAMPLE 21

Preparation of 3-[2-(4-Acetyl-3-hydroxy-2-propylphenoxy)ethoxy]-propanoic acid semihydrate A mixture of 1.94 g of 1-(2,4-dihydroxy-3-propylphenyl)ethanone, 7.00 g of bis-2-bromoethyl ether and 1.70 g of anhydrous potassium carbonatein 25 ml of anhydrous acetone was stirred at reflux for 20 hours. The reaction mixture was filtered and the filtrate was concentrated in vacuo to an oil which was chromatographed on 250 g of silica gel. Elution with 5% ethyl acetate-toluene gave 2.66 g (77% yield) of 1-[4-[2-(2-bromoethoxy)ethoxy]-2-hydroxy-3-propylphenyl]ethanone as an oil. The low resolution mass spectrum gave the molecular ion peak at m/e 344.

A solution of 2.60 g of 1-[4-[2-(2-bromoethoxy)ethoxy]-2-hydroxy-3-propylphenyl]ethanone, 0.50 g of sodium cyanide and 1.13 g of sodium iodide in 50 ml of dimethyl formamide was stirred and heated at 80° for 6 hours. The solvent was removed in vacuo, water was added to the residue and the product was extracted with ether. The dried (over magnesium sulfate) extract was concentrated in vacuo to give 2.13 g of impure 3-[2-(4-acetyl-3-hydroxy-2-propylphenoxy)ethoxy]propanenitrile.

A solution of 1.96 g of crude 3-[2-(4-acetyl-3-hydroxy-2-propylphenoxy)ethoxy]propanenitrile in 40 ml of ether and 40 ml of methanol was cooled in an ice bath while hydrogen chloride gas was bubbled through the solution for 10 minutes. The solution was cooled in the ice bath for 1 hour and then left at 23° for 16 hours. Nitrogen was bubbled through the solution to remove some of the excess hydrochloric acid and then 20 ml of water was added. Saturated sodium bicarbonate solution was added to neutralize the hydrochloric acid and the ether layer was separated. The aqueous layer was extracted with ethyl acetate and the combined extract was washed with sodium bicarbonate solution, dried (over magnesium sulfate) and concentrated in vacuo to an oil. Chromatography on 170 g of silica gel and elution with 30% ethyl acetate-toluene gave 1.01 g of crude 3-[2-(4-acetyl-3-hydroxy-2-propylphenoxy)ethoxy]propanoic acid methyl ester. The low resolution mass spectrum showed the molecular ion at m/e 324.

A solution of 1.01 g of crude 3-[2-(4-acetyl-3-hydroxy-2-propylphenoxy)ethoxy]propanoic acid methyl ester in 15 ml of methanol and 15 ml of 1.0N sodium hydroxide was stirred at 23° for 7 hours. The methanol was removed in vacuo, the residue was acidified and the product was extracted with ethyl acetate. The dried (over magnesium sulfate) extract was concentrated in vacuo to a solid which was recrystallized from ether-hexane to give 0.71 g, mp 48°-50°, of 3-[2-(4-acetyl-3-hydroxy-2-propylphenoxy)ethoxy]propanoic acid semihydrate.

Analysis Calculated for $C_{16}H_{22}O_6 \cdot 0.5H_2O$: C, 60.17; H, 7.26; $H_2O$, 2.82. Found: C, 60.07; H, 7.42; $H_2O$, 2.53.

EXAMPLE 22

3-[2-[2-[2-(4-Acetyl-3-hydroxy-2-propylphenoxy)ethoxy]ethoxy]ethoxy]propanoic acid semihydrate A mixture of 1.94 g of 1-(2,4-dihydroxy-3-propylphenyl, ethanone, 10 g of 1,11-dibromo-3,6,9-trioxaundecane and 1.7 g of anhydrous potassium carbonate in 25 ml of anhydrous acetone was stirred at reflux for 20 hours. The reaction mixture was filtered and the filtrate was concentrated in vacuo to an oil which was purified by high pressure liquid chromatography using 25% ethyl acetate-hexane to give 2.23 g (52% yield) of 1-[4-[2-[2-[2-(2-bromoethoxy)ethoxy]ethoxy]ethoxy]-2-hydroxy-3-propylphenyl]ethanone. The low resolution mass spectrum showed the molecular ion peak at m/e 432.

A solution of 2.23 g of 1-[4-[2-[2-[2-(2-bromoethoxy)ethoxy]ethoxy]ethoxy]-2-hydroxy-3-propylphenyl]ethanone, 0.34 g of sodium cyanide and 0.77 g of sodium iodide in 40 ml of dimethyl formamide was stirred and heated at 80° for 70 minutes. The solvent was removed in vacuo, water was added to the residue and the product was extracted with ether. The dried (over magnesium sulfate) extract was concentrated in vacuo to give 1.93 g of crude 3-[2-[2-[2-(4-acetyl-3-hydroxy-2-propylphenoxy)ethoxy]ethoxy]ethoxy]propanenitrile. The low resolution mass spectrum showed the molecular ion at m/e 379.

A solution of 1.93 g of crude 3-[2-[2-[2-(4-acetyl-3-hydroxy-2-propylphenoxy)ethoxy]ethoxy]ethoxy]-propanenitrile in 40 ml of ether and 40 ml of methanol was cooled in an ice bath while hydrogen chloride was bubbled through the solution for 10 minutes. The solution was kept in the ice bath for 1.5 hours and at 23° for 2 hours. Nitrogen was bubbled through to remove some of the excess hydrochloric acid and then 20 ml of water was added. Solid sodium bicarbonate was added to neutralize the hydrochloric acid and the product was extracted with ethyl acetate after saturating the aqueous layer with sodium chloride. The dried (over magnesium sulfate) extract was concentrated in vacuo to yield 1.91 g of crude 3-[2-[2-[2-(4-acetyl-3-hydroxy-2-propylphenoxy)ethoxy]ethoxy]ethoxy]propanoic acid methyl ester.

A solution of 1.91 g of 3-[2-[2-[2-(4-acetyl-3-hydroxy-2-propylphenoxy)ethoxy]ethoxy]ethoxy]propanoic acid methyl ester in 30 ml of methanol and 23 ml of 1.0N sodium hydroxide was stirred at 23° for 17 hours. The methanol was removed in vacuo, the residue was acidified and the product was extracted with ethyl acetate. The dried (over magnesium sulfate) extract was concentrated in vacuo to an oil (1.60 g) which was chromatographed on 170 g of silica ge. Elution with 10% acetic acid:25% ethyl acetate:65% toluene gave 1.28 g of 3-[2-[2-[2-(4-acetyl-3-hydroxy-2-propylphenoxy)ethoxy]ethoxy]ethoxy]propanoic acid semihydrate.

Analysis Calculated for $C_{20}H_{38}O_8 \cdot 0.5H_2O$: C, 58.95; H, 7.67; $H_2O$, 2.21. Found: C, 59.61; H, 7.63; $H_2O$, 2.16.

EXAMPLE 23

Preparation of 7-(4-Acetyl-3-hydroxy-2-propylphenoxy)heptanoic acid

A mixture of 5.8 g of 1-(2,4-dihydroxy-3-propylphenyl)ethanone, 5.4 ml of 7-bromoheptanenitrile and 8.3 g of anhydrous potassium carbonate in 50 ml of dimethyl formamide was stirred and heated at 75° for 20 hours. The reaction mixture was filtered and the filtrate was concentrated on the oil pump. The residual oil was chromatographed on 200 g of silica gel using 5% ethyl acetate-toluene to give 7.5 g (83% yield) of 7-(4-acetyl-3-hydroxy-2-propylphenoxy)heptane nitrile. This was dissolved in 200 ml of ether-methanol (1:1) and cooled in an ice bath while a stream of hydrochloric acid gas was introduced for 10 minutes. The reaction mixture was kept at 3° for 1 hour and at room temperature for 16 hours. Water (40 ml) was added and most of the solvent was removed in vacuo. The residue was treated with sodium bicarbonate solution to basify and the product was extracted with ether. The crude product was dissolved in 140 ml of methanol, treated with 120 ml of 1N sodium hydroxide and the solution was heated on the steam bath for 10 minutes and left at room temperature for 66 hours. The methanol was removed in vacuo and the aqueous solution was extracted with ether. The basic aqueous layer was acidified and extracted with ether. The dried (over magnesium sulfate) extract was concentrated and chromatographed on 50 g of silica gel. Elution with acetic acid (5): ethyl acetate (25): toluene (70) and crystallization of the combined pure fractions from ether-hexane gave 2.20 g, mp 64°–66°, of 7-(4-acetyl-3-hydroxy-2-propylphenoxy)heptanoic acid.

Analysis Calculated for $C_{18}H_{26}O_5$: C, 67.06; H, 8.13. Found: C, 67.08; H, 7.97.

EXAMPLE 24

| | CAPSULE FORMULATION | | | |
|---|---|---|---|---|
| | mg/capsule | | | |
| Ingredients | 25 mg | 50 mg | 100 mg | 200 mg |
| 6-(4-acetyl-3-hydroxy-2-propylphenoxy)-hexanoic acid | 25 | 50 | 100 | 200 |
| Lactose | 375 | 155 | 200 | 140 |
| Starch | 30 | 30 | 35 | 40 |
| Talc | 20 | 15 | 15 | 20 |
| Weight of capsule | 450 mg | 250 mg | 350 mg | 400 mg |

Procedure:
Mill 6-(4-acetyl-3-hydroxy-2-propylphenoxy)hexanoic acid, lactose and starch in a suitable mixer. Mill. Add talc and mix well. Encapsulate on suitable equipment.

EXAMPLE 25

| | TABLET FORMULATION | | | |
|---|---|---|---|---|
| | (Wet granulation) | | | |
| | mg/tablet | | | |
| Ingredients | 25 mg | 50 mg | 100 mg | 200 mg |
| 6-(4-acetyl-3-hydroxy-2-propylphenoxy)-hexanoic acid | 25 | 50 | 100 | 200 |
| Lactose | 280 | 153 | 187 | 171 |
| Modified Starch | 55 | 25 | 35 | 45 |
| Pregelatinized Starch | 35 | 20 | 25 | 30 |
| Distilled water q.s. | — | — | — | — |
| Magnesium Stearate | 5 | 2 | 3 | 4 |
| Weight of tablet | 400 mg | 250 mg | 350 mg | 450 mg |

Procedure:
Mix, 6-(4-acetyl-3-hydroxy-2-propylphenoxy)hexanoic acid, lactose, modified starch and pregelatinized starch in a suitable mixer. Granulate with sufficient distilled water to proper consistency. Mill. Dry in a suitable oven. Mill and mix with magnesium stearate for 3 minutes. Compress on a suitable press equipped with appropriate punches.

EXAMPLE 26

| TABLET FORMULATION | |
|---|---|
| (Direct Compression) | |
| Ingredients | mg/tablet |
| 6-(4-acetyl-3-hydroxy-2-propylphenoxy)hexanoic acid | 25 |
| Lactose | 181 |
| Avicel | 55 |
| Direct Compression Starch | 35 |
| Magnesium Stearate | 4 |
| Weight of Tablet | 300 mg |

Procedure:
Mix 6-(4-acetyl-3-hydroxy-2-propylphenoxy)hexanoic acid, with an equal amount of lactose. Mix well. Mix with avicel and direct compression starch, and the remaining amount of lactose. Mix well. Add magnesium stearate and mix for 3 minutes. Compression on a suitable press equipped with appropriate punches.

We claim:

1. A compound of the formula

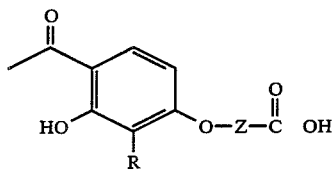

wherein R is hydrogen or lower alkyl, Z is —C*H$_2$—CH$_2$—CH$_2$—C≡C—, —C*H$_2$—C≡C—(CH$_2$)$_3$—, and —[(CH$_2$)$_2$O]$_n$(CH$_2$)$_2$— wherein n is an integer of 1 to 3, the carbon atom marked with an asterisk is linked to the phenoxy moiety,
or a salt thereof with a pharmaceutically acceptable base.

2. A compound, in accordance with claim 1, wherein R is hydrogen.

3. A compound, in accordance with claim 1, wherein R is lower alkyl.

4. A compound, in accordance with claim 3, wherein Z is —C*H$_2$—CH$_2$—CH$_2$—C≡C—.

5. A compound, in accordance with claim 3, wherein Z is —C*H$_2$—C≡C—(CH$_2$)$_3$—.

6. A compound, in accordance with claim 3, wherein Z is —[(CH$_2$)$_2$O]$_n$(CH$_2$)$_2$— and n is an integer of 1 to 3.

7. A compound in accordance with claim 3, 6-(4-acetyl-3-hydroxy-2-propylphenoxy)-5-heptynoic acid.

8. A compound in accordance with claim 3, 6-(4-acetyl-3-hydroxy-2-propylphenoxy)-2-hexynoic acid.

9. A pharmaceutical composition comprising a compound of the formula

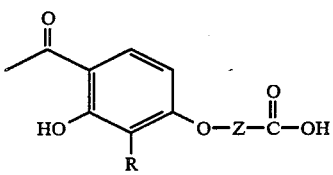

wherein R is hydrogen or lower alkyl, Z is —C*H$_2$—CH$_2$—CH$_2$—C≡C—, —C*H$_2$—C≡C—(CH$_2$)$_3$—, and —(CH$_2$)$_2$O]$_n$(CH$_2$)$_2$— wherein n is an integer of 1 to 3, the carbon atom marked with an asterisk is linked to the phenoxy moiety,
or a salt thereof with a pharmaceutically acceptable base, an inert pharmaceutical carrier.

10. A pharmaceutical composition, in accordance with claim 9, wherein R is lower alkyl.

11. A pharmaceutical composition in accordance with claim 13, 7-(4-acetyl-3-hydroxy-2-propylphenoxy)-5-heptynoic acid.

12. A pharmaceutical composition in accordance with claim 13, 6-(4-acetyl-3-hydroxy-2-propylphenoxy)-2-hexynoic acid.

13. A method of treating allergic conditions in which slow reacting substance of anaphylaxis is a mediator which comprises administering an effective amount of a compound of the formula

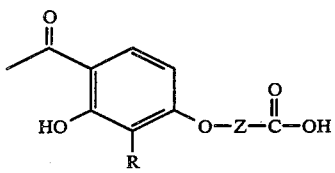

wherein R is hydrogen or lower alkyl, Z is —C*H$_2$—CH$_2$—CH$_2$—C≡C—, —C*H$_2$—C≡C—(CH$_2$)$_3$—, and —(CH$_2$)$_2$O]$_n$(CH$_2$)$_2$— wherein n is an integer of 1 to 3, the carbon atom marked with an asterisk is linked to the phenoxy moiety,
or a salt thereof with a pharmaceutically acceptable base.

14. A method, in accordance with claim 13, wherein R is lower alkyl.

15. A method, in accordance with claim 13, 7-(4-acetyl-3-hydroxy-2-propylphenoxy)-5-heptynoic acid.

16. A method in accordance with claim 13, 6-(4-acetyl-3-hydroxy-2-propylphenoxy)-2-hexynoic acid.

17. A compound in accordance with claim 3, 3-[2-(4-acetyl-3-hydroxy-2-propylphenoxy)ethoxy]propanoic acid semihydrate.

18. A compound in accordance with claim 3, 3-[2-[2-[2-(4-acetyl-3-hydroxy-2-propylphenoxy)ethoxy]ethoxy]ethoxy]propanoic acid semihydrate.

19. A pharmaceutical composition in accordance with claim 9, 3-[2-(4-acetyl-3-hydroxy-2-propylphenoxy)ethoxy]propanoic acid semihydrate.

20. A pharmaceutical composition in accordance with claim 9, 3-[2-[2-[2-(4-acetyl-3-hydroxy-2-propylphenoxy)ethoxy]ethoxy]ethoxy]propanoic acid semihydrate.

21. A method in accordance with claim 13, 3-[2-(4-acetyl-3-hydroxy-2-propylphenoxy)ethoxy]propanoic acid semihydrate.

22. A method in accordance with claim 13, 3-[2-[2-[2-(4-acetyl-3-hydroxy-2-propylphenoxy)ethoxy]ethoxy]ethoxy]propanoic acid semihydrate.

* * * * *

UNITED STATES PATENT AND TRADEMARK OFFICE
CERTIFICATE OF CORRECTION

PATENT NO.  : 4,628,115
DATED       : December 9, 1986
INVENTOR(S) : Matthew Carson, Ronald A. LeMahieu, William C. Nason It is certified that error appears in the above-identified patent and that said Letters Patent is hereby corrected as shown below:

In Claim 7, line 1, "6-(4-acetyl..." should read as
-- 7-(4-acetyl... --

In Claim 9, line 46, "$-(CH_2)_2O]_n(CH_2)_2$ should be
-- $[(CH_2)_2O]_n(CH_2)_2$ In Claim 13, line 22, "$-(CH_2)_2O]_n(CH_2)_2$" should be
-- $[(CH_2)_2O]_n(CH_2)_2$ --

Signed and Sealed this

Thirtieth Day of August, 1988

Attest:

DONALD J. QUIGG

*Attesting Officer*         *Commissioner of Patents and Trademarks*